United States Patent [19]

Feist et al.

[11] Patent Number: 4,747,295
[45] Date of Patent: May 31, 1988

[54] TEST PIECE FOR ULTRASONIC TESTING

[75] Inventors: Wolf-Dieter Feist, Rettenbach; Manfred Podlech, Hebertshausen; Johann Gollwitzer, Jetzendorf, all of Fed. Rep. of Germany

[73] Assignee: MTU Motoren- und Turbinen-Union München GmbH, Munich, Fed. Rep. of Germany

[21] Appl. No.: 919,003
[22] PCT Filed: Jan. 21, 1986
[86] PCT No.: PCT/DE86/00017
 § 371 Date: Nov. 25, 1986
 § 102(e) Date: Nov. 25, 1986
[87] PCT Pub. No.: WO86/04415
 PCT Pub. Date: Jul. 31, 1986

[30] Foreign Application Priority Data

Jan. 25, 1985 [DE] Fed. Rep. of Germany ....... 3502454

[51] Int. Cl.$^4$ ...................... G01D 18/00; G01N 29/04
[52] U.S. Cl. ..................................... 73/1 DV; 29/407
[58] Field of Search ............... 73/1 DV, 1 R; 367/13; 29/407

[56] References Cited

U.S. PATENT DOCUMENTS

| | | | |
|---|---|---|---|
| 4,173,139 | 11/1979 | Conn | 73/1 DV |
| 4,203,315 | 5/1980 | Vicu et al. | 73/1 DV X |
| 4,233,720 | 11/1980 | Rozmus | 29/407 |
| 4,266,270 | 8/1984 | Kimura et al. | 73/1 DV X |
| 4,309,904 | 1/1982 | Jones et al. | 73/1 DV X |
| 4,331,021 | 5/1982 | Lopez et al. | 73/1 DV |
| 4,361,044 | 11/1982 | Kuppermon et al. | 73/1 DV X |
| 4,406,153 | 9/1983 | Ophir et al. | 73/1 DV |
| 4,417,582 | 11/1983 | Trimmer et al. | 73/1 DV X |
| 4,466,270 | 8/1984 | Kimura et al. | 73/1 DV X |
| 4,475,376 | 10/1984 | Keilmon | 73/1 DV |

FOREIGN PATENT DOCUMENTS 2814336 5/1979 Fed. Rep. of Germany .

OTHER PUBLICATIONS

*Patents Abstracts of Japan*; vol. 9, No. 93, p. 351 (1816); Apr. 23, 1985; (English Abstract of Japanese Patent Document No. 59-221662, published Dec. 13, 1984, An Inventor of Hideki Kobayashi).

*Primary Examiner*—Tom Noland
*Attorney, Agent, or Firm*—Barnes & Thornburg

[57] ABSTRACT

A device is provided for ultrasonic testing, particularly for monitoring the measuring precision and the calibrating of high resolution ultrasonic testing apparatus or ultrasonic testing heads. The device includes a powder-metallurgically produced test piece element. The test piece element includes insert elements immovably fixed to an interior surface of a capsule. Powder is provided in the capsule which is poured to surround the immovably fixed insert elements. The powder is subjected to changed temperature and pressure thereby forming the test piece. A process for producing the apparatus is also provided.

20 Claims, 1 Drawing Sheet

U.S. Patent
May 31, 1988
4,747,295
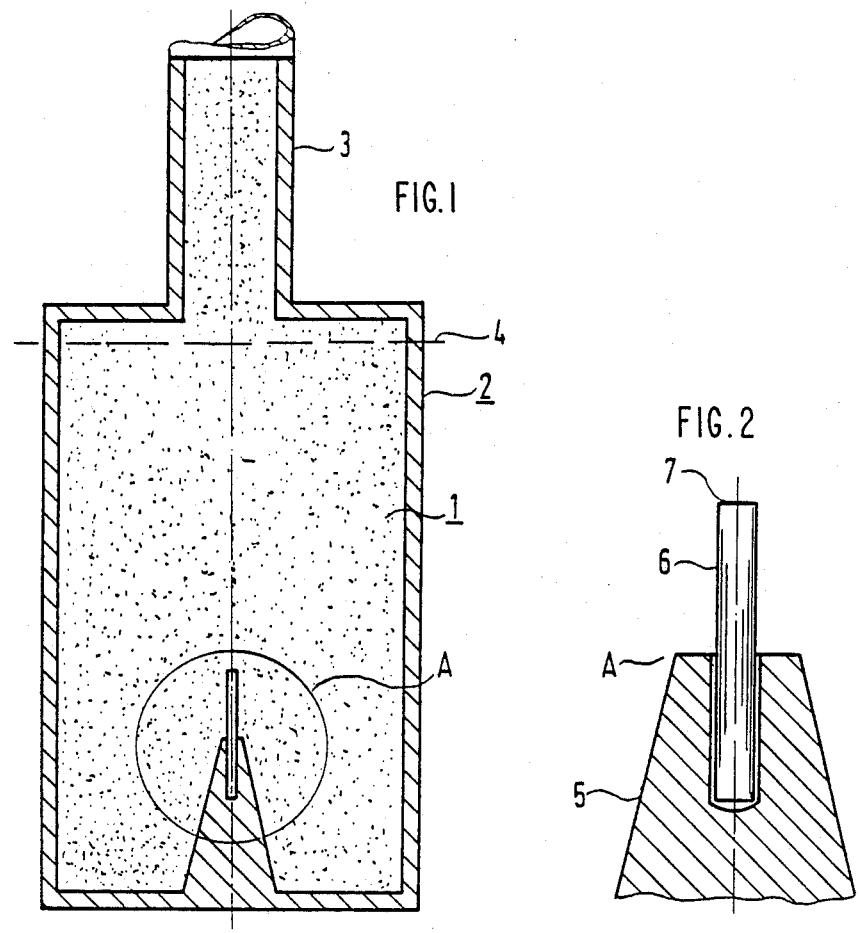
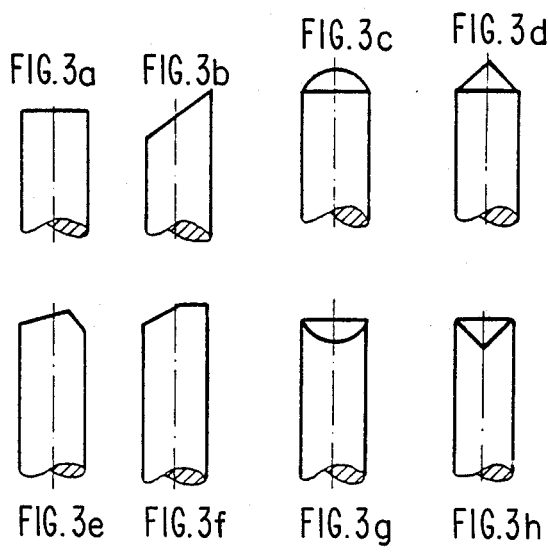

TEST PIECE FOR ULTRASONIC TESTING

BACKGROUND AND SUMMARY OF THE INVENTION

This invention relates to a test piece for ultrasonic testing having a test defect or test reflector of a certain type, position and size for the testing or calibration of ultrasonic testing apparatus or ultrasonic testing heads.

The invention is intended for use in nondestructive material testing.

For the calibrating of ultrasonic testing apparatus and/or testing heads and for identifying and recognizing a defect test reflectors or small test defects are required. Circular-disk reflectors are known, for example, in the form of pocket bores with a flat bottom. However, bores of this type cannot be made arbitrarily small, especially when the bottom is to be flat.

On the other hand, with the increasing exhaustion of the stability potentials of new materials, such as powder metal superalloys or highly stable ceramics, it is necessary to detect increasingly small defects in the material. As a result, a miniaturization of the ultrasonic testing technology is required.

It is an objective of the invention to provide a test piece having a very small test defect $\phi \leqq 0.5$ mm so that it can be reproduced with respect to position and sound behavior. Also, the test piece must be easily produced and must contain a reflector of any shape that must, however, be able to be reproduced.

This objective is achieved by means of a test base for ultrasonic testing having a test defect or test reflector of a predetermined configuration, position and size for the testing or the calibration of ultrasonic testing apparatus and ultrasonic testing heads comprised of inserts forming the test defect that, with their largest longitudinal dimension are arranged in acoustic irradiation direction and have a reflection surface for the generating of an ultrasonic echo that is no larger than about 0.2 square millimeters and faces the surface of the test piece against which the test head rests during the ultrasonic testing period.

It is another object of the invention to create a test piece wherein the reflection surface of the insert has a fixed distance to the surface serving as the contact surface for the test head.

It is another object of the invention to create a test piece wherein the reflection surface is convex or concave in the direction of the sound.

It is another object of the invention to practice a method of forming a test piece according to a power-metallerical step such as an isostatic cold and/or hot compacting.

It is another object of the invention to produce a test piece comprised of pulverizable metal, intermemtallic phases or ceramics.

It is another object of the invention to produce a test piece containing an insert or inserts compacted in a rod shaped, needle shape or fiber shape.

It is another object of the invention to produce a test piece comprising inserts of quartz glass, diamond or sapphire.

It is another object of the invention to produce a test piece having inserts which have a reflection surface arranged symmetrically around an axis and in certain embodiments are conical.

It is another object of the invention to produce a test piece wherein reflection surfaces are of assymetrical symmetrical shape.

It is another object of the invention to produce a test piece wherein the reflection surface is composed of slanted or partial surfaces.

The invention makes it possible to produce a test piece having replacement defects and/or replacement reflectors (inserts) of a magnitude of about 0.01 to 0.05 mm that can be reproduced and are defined geometrically within narrow limits. The invention also makes it possible to produce reflectors in almost arbitrarily reproduceable shapes and to determine related influences on the ultrasonic signal. The test piece, in this case, consists of pulverizable metal, intermetallic phases or ceramics. The inserts advantageously consist of quartz glass or a material with a similar behavior.

The foregoing and other objects, features, and advantages of the present invention will become more apparent from the following description when taken in connection with the accompanying drawings which show, for the purposes of illustration only, plural embodiments in accordance with the present invention, and wherein:

BRIEF DESCRIPTION OF THE INVENTION

FIG. 1 is the test piece with the insert arranged in it,
FIG. 2 is the enlarged detail A from FIG. 1; and
FIGS. 3(a) to (h) are various developments of the reflector surface.

Referring now to the drawings wherein like reference numerals are used to designate like parts and more particularly to FIG. 1 which shows a test piece 1, in this case, a compact, which is contained in a capsule 2. The capsule 2 has a feeding tube 3 into which metal powder, for example, Ni base alloy, advantageously of a grain size $< 100$ $\mu$m, an intermetallic phase or a ceramic powder is fed. After a compacting process (hot-isostatically or cold-isostatically) the feeding tube 3 and a lid are removed, and the compact is ground off, for example. The ground surface will then form the later surface 4 of the test piece. As shown in FIG. 2, in the bottom area of the compact 1, an insert holder 5, FIG. 2, and insert 6, such as a quartz rod, are fastened. The insert has, for example, a reflector surface 7 that is located in a parallel plane with respect to the surface 4 of the test piece. By means of this replacement reflector 7 or replacement defect, the desired tests can be carried out on ultrasonic apparatus. The acoustic irradiation direction, in the shown embodiment, is in downward direction, i.e. in vertical direction or in planes that are in parallel to the axis of the compact. In this case, the test piece is normally dipped into a liquid.

The following is an example of the manufacturing process of the test piece.

The insert or inserts 6 made of material that does not interfere with the ultrasonic testing, such as quartz glass or synthetic diamond material, or sapphire material, in rod shape, needle shape or fiber shape of about 10–100 $\mu$m $\phi$ in a lump or particle with an arbitrary surface development (see FIG. 3) is (are) held in a defined geometrical position (according to FIG. 1) in the (Fe-) capsule 2 by means of the holding element 5 at the bottom of the capsule 2, for example, at a distance of 1–10 mm from surface 4 when the capsule 2 has a 100 of about 20 mm and a length of about 30–60 mm.

Subsequently, the metal powder is fed in through the feeding pipe or a feeding funnel. During this process, the inserts 7 must not be displaced from the previously described position. For this reason, the holding element 5 of the inserts 7 such as quartz rods, at the capsule, particularly at the capsule bottom, are developed in such a way, advantageously conically, that no one-sided forces during the compacting process, such as, for example, cold-isostatical or hot-isostatical compacting, affect the insert 7, such as the quartz rod. During the feeding process of the capsule 2 with powder material, the capsule 2 is advantageously evacuated and is subsequently closed, for example, when the capsule 2 consists of metal, by means of welding, so that it is tight. The powder may also be fed in by air and can be evacuated subsequently,-before the closing. Then the compacting process is started. It may take place in a compacting press that is customary for the previously mentioned processes, and at the customary pressures and temperatures. In addition, one or several heat treatment stages may also follow the compacting process.

Subsequently, the decapsulating takes place by the separating of the feeding tube with the lid. The nominal length in the case of surface 4 is adjusted by a treatment process that is known per se. The insert must be firmly enclosed.

The test piece consists of a material that is identical with or similar to the material or workpiece to be tested. It is necessary to use such materials or material groups that can be processed according to a powder metallurgical method.

The selection of material for the insert or inserts 6 such as rods, needles and fibers, depends on the compacting temperature, particularly the HIP-temperature (HIP=hot isostatic compacting) of the test piece material and depends on the desired acoustical impedance differences. Quartz, for example, is suitable for the insertion in nickel base alloys, because it can be used advantageously, for example, during hot compacting. In the case of the HIP temperature for such an alloy, the insert is so firm that the shape is maintained and a sufficient impedance difference exists to the surrounding material made of the alloy. Other correspondingly suitable pairings of materials may also be selected.

For the ultrasonic testing, a high-resolution and in proportion to the desired resolution high-focussing testing head of a corresponding wave length and corresponding power, for example, between 5 to 50 mc/s, particularly 25 mc/s, is preferred. The testing head that is not shown is brought to rest against the surface 4 of the immersed test piece 1 that was finally ground to the desired measurement (nominal length).

While we have shown and described embodiments in accordance with the present invention, it is understood that the same is not limited thereto but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. Device for ultrasonic testing, particularly for monitoring the measuring precision and the calibrating of at least one of high resolution ultrasonic testing apparatus and ultrasonic testing heads, of the type including a powder-metallurgically produced test piece means, said test piece means comprising:
   a capsule having an interior for receiving powder;
   insert means immovably fixed to said interior of said capsule for providing one of a reference defect and a reference reflector; and
   powder poured in said capsule surrounding said immovably fixed insert means, said powder being subjected to changed temperature and pressure thereby forming said test piece.

2. Device as in claim 1, wherein said insert means is fixed to said capsule such that said insert means has a first dimension parallel to a direction sound applied to said test piece and a second dimension forming a reflection surface.

3. Device as in claim 2, wherein said first dimension is larger than said second dimension.

4. Device as in claim 2, wherein said test piece further includes a testing surface against which said testing head is placed during ultrasonic testing, said fixed insert reflection surface facing said testing surface.

5. Device as in claim 4, wherein said capsule includes a floor surface facing said testing surface, said insert means being fixed to said floor surface.

6. Device as in claim 5, further including conical holding means for holding said insert means in a fixed predetermined position.

7. Device as in claim 2, including an isostatic cold pressed, powder-metallurgically produced test piece.

8. Device as in claim 2, including an isostatic hot pressed, powder-metallurgically produced test piece.

9. Device as in claim 2, wherein said test piece is made of one of pulverizable metal, intermetallic phases and ceramics.

10. Device as in claim 2, wherein said insert means includes a shape of one of a rod, a needle and a fiber.

11. Device as in claim 10, wherein said insert means is made of one of quartz glass, diamond and sapphire.

12. Device as in claim 2, wherein said insert has an insert axis through said first dimension, said reflection surface being symmetrical around said insert axis.

13. Device as in claim 12, wherein said reflection surface is an acute cone.

14. Device as in claim 2, wherein said insert means includes at least one slanted surface at said reflection surface.

15. Device as in claim 2, wherein said reflection surface is convex with respect to said insert means.

16. Device as in claim 2, wherein said reflection surface is concave with respect to said insert means.

17. Device as in claim 2, wherein said insert has an insert axis through said first dimension, said reflection surface including surfaces arranged assymetrically with respect to said insert axis.

18. Device as in claim 2, wherein said insert means includes at least two slanted surfaces having different sizes at said reflection surface.

19. Process for powder-metallurgically producing a test piece device for ultrasonic testing, particularly for monitoring the measuring precision and the calibrating of one of high resolution ultrasonic testing apparatus and ultrasonic testing heads, comprising:
   immovably fixing insert means at a predetermined point of an interior wall of a capsule;
   filling said capsule with powder; and
   hermetically closing said capsule and subjecting said powder to changed temperature and pressure.

20. Process as in claim 19, wherein said powder in said hermetically closed capsule is subjected to one of isostatic cold pressing and isostatic hot pressing.

* * * * *